United States Patent
Apfelbaum et al.

[11] Patent Number: 5,928,233
[45] Date of Patent: Jul. 27, 1999

[54] SPINAL FIXATION DEVICE WITH LATERALLY ATTACHABLE CONNECTORS

[75] Inventors: Ronald I. Apfelbaum, Salt Lake City, Utah; Charles E. Dinkler, II, Cincinnati, Ohio

[73] Assignee: Ohio Medical Instrument Co., Inc., Cincinnati, Ohio

[21] Appl. No.: 08/821,170

[22] Filed: Mar. 21, 1997

Related U.S. Application Data

[63] Continuation of application No. 08/577,804, Dec. 22, 1995, abandoned.

[51] Int. Cl.⁶ ................................................... A61B 17/58
[52] U.S. Cl. ................................................ 606/61; 623/17
[58] Field of Search ........................... 606/60–61, 69–73; 623/16–17

[56] References Cited

U.S. PATENT DOCUMENTS

| | | | |
|---|---|---|---|
| 4,269,178 | 5/1981 | Keene | 606/61 |
| 4,289,123 | 9/1981 | Dunn | 623/17 |
| 5,024,213 | 6/1991 | Asher et al. . | |
| 5,053,034 | 10/1991 | Olerud . | |
| 5,084,049 | 1/1992 | Asher et al. . | |
| 5,127,912 | 7/1992 | Ray et al. . | |
| 5,133,717 | 7/1992 | Chopin . | |
| 5,254,118 | 10/1993 | Mirkovic . | |
| 5,300,073 | 4/1994 | Ray et al. . | |
| 5,312,404 | 5/1994 | Asher et al. . | |
| 5,360,429 | 11/1994 | Jeanson et al. | 606/61 |
| 5,397,363 | 3/1995 | Gelbard | 606/72 |
| 5,403,314 | 4/1995 | Currier . | |
| 5,474,551 | 12/1995 | Finn et al. | 606/61 |
| 5,476,463 | 12/1995 | Boachie-Adjei et al. | 606/61 |
| 5,498,262 | 3/1996 | Bryan | 606/61 |

FOREIGN PATENT DOCUMENTS

WO 9314721  8/1993  WIPO .
WO9428831  12/1994  WIPO .

OTHER PUBLICATIONS

AESCULAP Brochure, "Micro, Neuro and Spine Surgery"—CASPAR Instruments for Anterior Cervical Fusion.

*Primary Examiner*—Paul B. Prebilic
*Assistant Examiner*—Francis K. Cuddihy
*Attorney, Agent, or Firm*—Wood, Herron & Evans, L.L.P.

[57] ABSTRACT

A spinal fixation device includes a threaded stud having an open-ended axial slot to straddle a rod of a vertebral support, and a bracket which is rotatable on the stud. A vertebra bone screw passes through an opening in a distal end of the bracket. The stud and bracket are locked in position relative to the rod by a nut. An insert within the slot bears against the rod and prevents the stud from being deformed by the force of the nut on the stud segments. The bracket can be rotated around the stud; and the stud can be rotated around and slid along the rod, to afford great adjustability and ease of attachment.

16 Claims, 2 Drawing Sheets

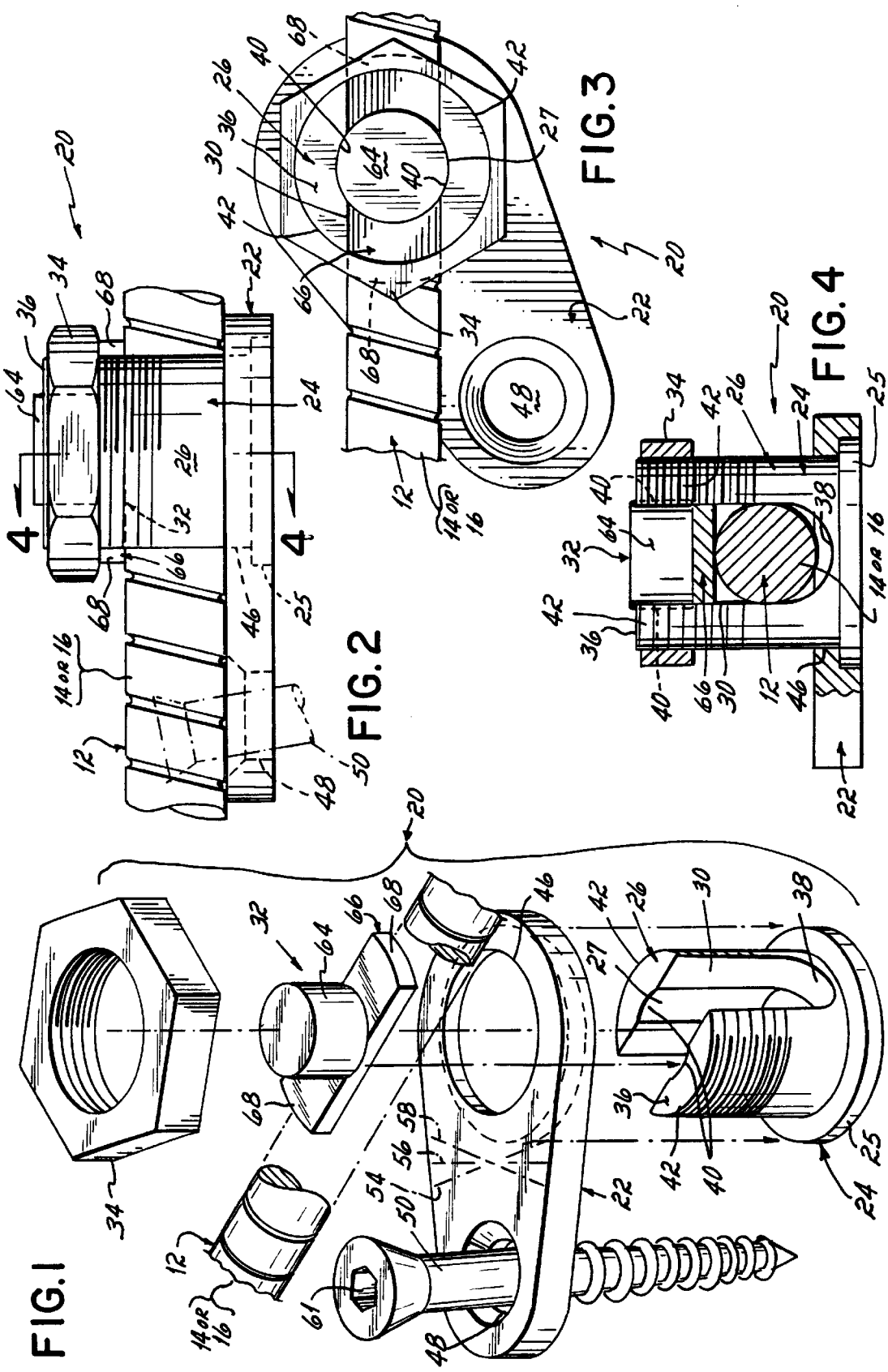

5,928,233

SPINAL FIXATION DEVICE WITH LATERALLY ATTACHABLE CONNECTORS

This application is a continuation of application Ser. No. 08/577,804, filed on Dec. 22, 1995, now abandoned.

FIELD OF THE INVENTION

This invention relates to a "spinal fixation device", that is, a device for securing vertebrae of the upper spine of a patient in desired positions in relation to one another and/or to the skull.

BACKGROUND OF THE INVENTION

Fixation devices are used in many surgical procedures, for example to secure vertebral fractures during healing, and to fuse damaged vertebrae against movement. Such devices typically include a longitudinal support such as a rod or U-shaped member which is shaped to fit along the spinal column; a hook, clamp or screw type fastener which engages a vertebra; and a bracket or connector which interconnects the fastener to the longitudinal support. All three types of fasteners -hook, clamp, and screw—are widely used for fixation of the thoracic and lumbar regions (i.e., below the cervical vertebrae) where there are relatively large vertebral bone structures to carry the load. In those regions, fasteners of the hook and clamp types can be hooked over or engaged with posterior elements of the vertebrae or lateral projections. Large so-called "pedicle screws," which have coarse threads and are roughly similar to a lag screw are also used in the lumbar and thoracic regions. They extend from a bracket down the pedicle of the vertebra and into the vertebral body.

However, it is more difficult to attach hooks, clamps and screws in upper spine areas, that is, in the thoracic and cervical areas, because there the bone anatomy becomes progressively smaller. There is not adequate space or bone mass to secure pedicle screws, which are too large; and hooks sometimes tend to work loose in this area because of the hypermobility of the spine.

To achieve fixation in the cervical spine, the most common posteriorly used fixation devices are what are known as lateral mass plates. Screws are used to secure these but are much smaller than the pedicle screws used in lower thoracic and lumbar spine fixations. The screws are driven into the lateral masses of the vertebral body through holes in a plate which vertically bridges sequential vertebral segments. The locations in which these screws can be placed are limited so that each screw must be placed in a closely defined ideal position. The device must accommodate the requirements of mounting each screw in a precisely selected location, because the screws cannot be forced into any other position.

To date, however, there has been no practical way of coupling these types of screw fixations, that is, to couple a device of the type suitable for cervical spine fixation with a support that allows either a rod type of construct for posterior cervical fusion or extension of a thoracic fusion across the cervicothoracic junction. The same lack of interchangeability between these two different types of constructs has also limited their application superiorly, that is, across the upper end of the spine, between the occipital bone of the skull and the cervical spine.

Thus there has been a need for a fixation device which will allow mating both lateral mass fixation screws and C1–C2 fixation screws with a rod-type support that can be combined with other types of fixation device at lower positions on the spine, for example, across the cervicothroracic junction.

In fixation devices of the screw type, the screw usually extends through a first opening in a bracket while the longitudinal support extends through a second opening in the bracket. U.S. Pat. Nos. 5,403,314 and 5,312,404 both disclose such apparatus. In those patents, once the bracket has been placed on the rod, it can be rotated about one axis only, i.e., circumferentially around the rod. The bracket cannot be rotated about an axis perpendicular to the rod. Thus the angulation of the axis of the bracket is fixed with respect to the axis of the support rod. This makes it difficult to "aim" a screw if it is to be secured into a small area of a cervical vertebra.

Another disadvantage of the fixation devices of those patents is that the physician has to determine in advance the number of fasteners and connectors to be used for a particular surgical procedure, before the rod or rods are fixed in position along the spinal column, because connectors could be attached to a rod only by sliding them in sequence along the length of the rod. After the rod was secured to the spinal column, an additional or intermediate connector could not be slid onto the rod without first removing at least one end of the rod from connection to the spine of the patient. If some fasteners were already secured to vertebrae and more were needed, they could be added only by removing the secured fasteners or the entire device from the patient, so that they could be slid along the rod to the desired location.

It has been an objective of this invention to provide a system which mates a screw fixation technique for the cervical spine with a rod-type support which allows fixation to be extended either superiorly or interiorly on the spine.

It has been a further object of this invention to provide a fixation device for cervical spine use, having a bracket that is rotatable about multiple axes, so that the opening through which the fastener extends can be positioned in a wider range of orientations in relation to the rod, for precise screw orientation.

Another object of this invention has been to provide a bracket that may be mounted to a rod which has itself already been secured to the spinal column.

SUMMARY OF THE INVENTION

This invention provides a fastener having a bracket or connector which is adjustable about multiple axes with respect to a longitudinal support, so that a screw through it can be precisely positioned to engage a cervical or other vertebra. The bracket is movable on a connector which can be inserted laterally onto a rod of a vertebral support in situ, that is, directly onto the middle of an already mounted rod, as distinguished from being slid axially from an end of a rod before mounting to the spine.

In accordance with the invention the device includes a fastener bracket having first and second openings through it, one for a fastener such as a small bone screw to be secured to a vertebrae, the other opening for a stud (i.e., a post) by which the bracket can be connected to the rod of a vertebral support. The stud has an enlarged head and a threaded shank which extends through the second opening in the bracket so that the bracket is rotatable around the longitudinal axis of the stud. The shank of the stud is threaded but has a longitudinal (axial) slot which extends from the end of the stud partway toward the head. The slot lies between two threaded shank segments on opposite sides of the shank, like a tuning fork.

The vertebral support includes at least one rod or leg and is preferably U-shaped, having two spaced apart parallel rods connected by a generally semicircular middle section.

The connector assemblies can be mounted on one or two rods; often connectors will be mounted on both rods. The stud slot straddles the rod; that is, the rod extends crosswise through the slot. A clamping and spacing insert is seated in the slot of the stud for clamping the rod to the connector. The insert is preferably T-shaped, having a flange projecting from a stem. The stem of the insert fits axially in the slot between the shank segments, projecting away from the stud head. The flange of the insert extends laterally across the slot between the segments of the stud, parallel to the rod, and in use is held against the rod to clamp it against the slot end. A nut is threaded onto the two segments of the stud, and in use bears against the radially projecting ends of the flange of the insert to clamp it against the support rod in the slot. The stem of the insert holds the stud segments spaced apart as the nut is tightened, and has been found to prevent inward deformation or bending of the segments which otherwise could render it considerably more difficult to remove or adjust the connector.

One or more preassembled connectors can be slid along the rod to desired position, or they can be inserted laterally on the rod intermediate to other points of attachment. To do so the stem, with the insert and the nut removed, is placed so that the segments on either side of the slot straddle the rod. The insert is then placed in the slot, and the nut applied and tightened. This affords a substantial advantage in comparison to previous screw connectors of the type which had to be slid in longitudinal sequence onto the rod of the vertebral support.

Until the nut is tightened, the connector can be adjusted on three axes with respect to the rod: (1) it can be slid lengthwise along the rod to a desired vertical position; (2) it can be rotated around the axis of the rod; and (3) the bracket or tab can be rotated around the axis of the stud. Moreover, the angulation of the bone screw or other fastener through the bracket can be adjusted with respect to the bracket through which it extends. Also, the tab can be bent to closely conform to the bony anatomy.

The present invention thus allows for great flexibility in placing the stud which attaches to the support rods. This is a substantial advantage over systems in which one has to place pedicle screws (for example in the lumbar spine) and then try to contour the rod so that it will line up with the openings in each of the connectors. With this invention each screw can be placed in the ideal position for that vertebra, the bracket can then be pivoted in such a way that the receiving studs along the spine are in alignment. The rod, contoured only for anterior/posterior variations or desired anatomy, can be "dropped" into the slots and the screws secured, to achieve a fast and very good alignment.

In short, the invention is facile to use and results in an easy but secure connection to the rod, with much less practical difficulty.

DESCRIPTION OF THE DRAWINGS

The invention can best be further described by reference to the accompanying drawings in which, FIG. 1 is a fragmentary, enlarged and exploded perspective view of a preferred form of fixation device in accordance with the invention, showing one sequence in which its components can be assembled;

FIG. 2 is a side elevation of the assembled connector of FIG. 1;

FIG. 3 is a top plan view of the connector;

FIG. 4 is a vertical cross-section taken on line 4—4 of FIG. 2; and

DETAILED DESCRIPTION

Figure 5:
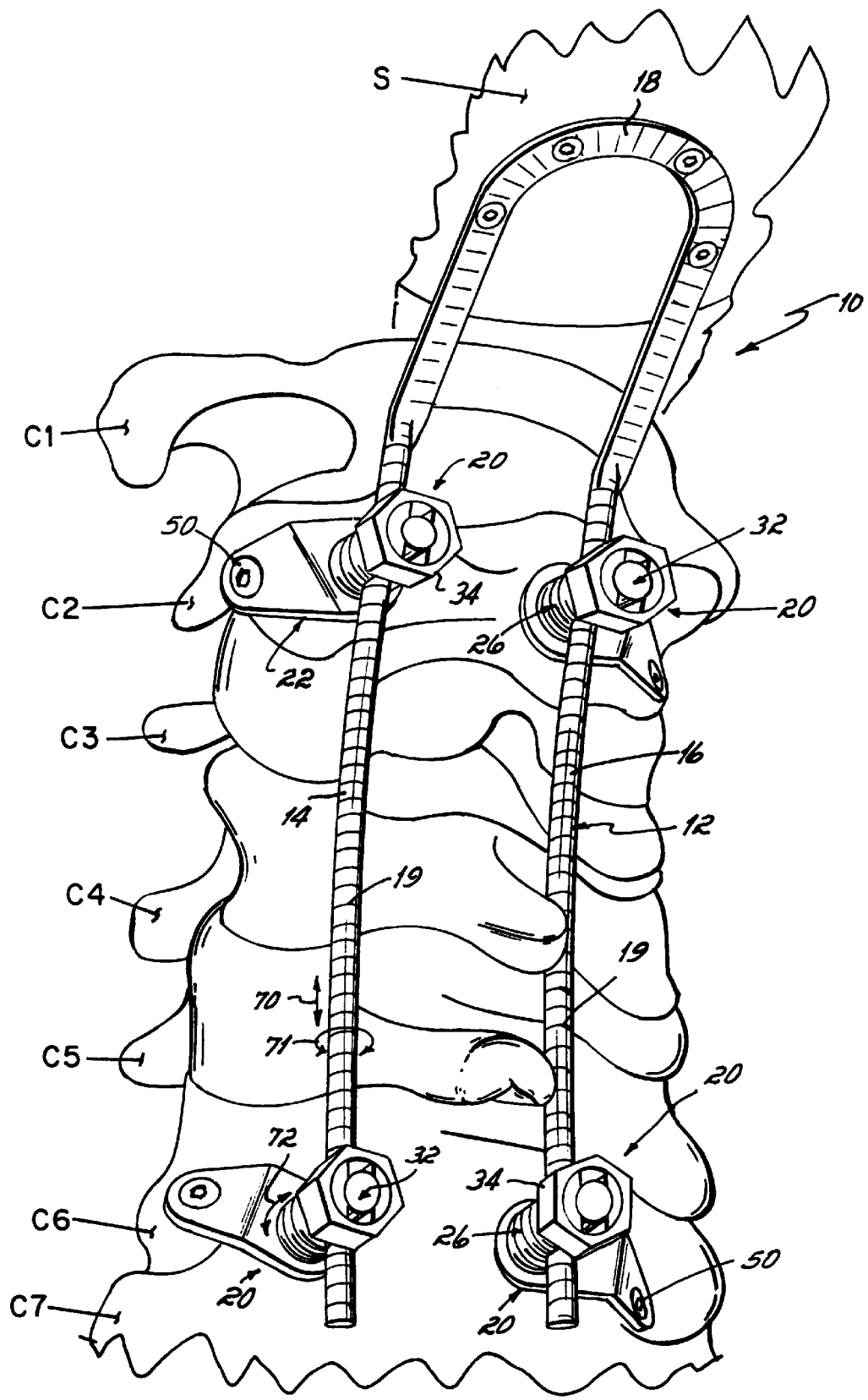
FIG. 5 is a perspective view, diagrammatic in nature, showing the invention being used to fixate the cervical spine and occipital bone of the skull of a patient.

Referring first to FIG. 5 of the drawings, there is shown the upper portion of a human spinal column comprising cervical vertebrae C1–C7 and the occipital bone S of the skull. A fixation device in accordance with this invention is designated generally by 10 and comprises a vertebral support 12, preferably having two spaced parallel rods in the form of legs 14, 16, extending along opposite sides of the vertebrae and connected at the top by a middle section 18. In the embodiment shown, vertebral support 12 is generally in the shape of an inverted "U" with its legs 14, 16 extending downwardly from a semicircular middle section 18 located adjacent the base of skull S. Rods or legs 14, 16 preferably have shallow spiral grooves 19 along them, which facilitate securing vertebral attachment wires (not shown) to them so that the wire cannot slip longitudinally. (Use of such wires is well known and does not comprise part of the invention.) Several connector assemblies 20, each in accordance with the invention, are mounted on the respective legs or rods 14, 16 of support 12. Although not shown in FIG. 5 for simplicity, a connector will usually be provided for and secured to each vertebra between the uppermost and lowermost vertebrae to be secured.

As best shown in FIGS. 1–4, each connector assembly 20 comprises a bracket 22 which is rotatable around the axis of a stud 24. The stud has a longitudinal (axial) slot 30 which straddles a rod or leg 14 or 16 of vertebral support 12. The leg can be clamped in slot 30 by a clamping and spacing insert 32 and a nut 34 screwed onto shank 26.

More specifically, stud 24 has a stopped axial bore 27 which extends from stud end 36 toward the enlarged or flanged head 25 of the stud. Slot 30 intersects and extends across bore 27, leaving only shallow longitudinal bore portions or channels 40, 40 which run longitudinally on the opposed faces of stud shank segments or sectors 42, 42 on each side of slot 30.

Bracket 22 has two openings through it, a larger diameter first opening 46 sized to rotatably receive the shank 26 of stud 24, and a second opening 48 which provides a seat for the head of a screw fastener 50. Screw 50 has a fastening shank 51 and a head slot or socket 61 for tightening with an Allen wrench or a screwdriver, and is adapted to be driven into bone. The head may be flared as shown or rounded to seat in the recessed opening 48 of bracket 22. Bracket 22 may be an essentially flat tab as shown in FIG. 1, or it may be canted or angulated along a transverse axis 54, 56, or 58 (shown in dashed lines in FIG. 1), to better orient or direct screw 50 in a desired direction toward the ideal vertebrae area into which it is to be driven. If bracket 22 is bent along either axis 54 or 58, the axes of openings 46 and 48 will not intersect. One face 63 of bracket 22 (the lower face in the drawings) may be counterbored (recessed) to receive the enlarged head 25 of stud 24. The opposite (upper) face 65 of the bracket may be recessed to receive the head of fastener 50. Thus, as viewed in FIGS. 1–4, the shank 26 of stud 24 extends upwardly above the upper face of bracket 22 while fastener 50 extends downwardly below the lower face.

Insert 32 is generally T-shaped, having a flange 66 and a generally cylindrical stem 64. The stem 64 is seated and axially slidable in stud slot channels 40, 40. The flange is sized to project laterally outwardly of slot 30 in stud 24. In use, one face of flange 66 (the lower face in FIG. 1) bears on the surface of rod 14 or 16 which passes through slot 30 over first opening 46 and the upper face 65 of bracket 22. When nut 34 is tightened on stud segments 42, 42, its face bears on projecting ends 68 of flange 66, urging flange 66 against leg 14 to clamp the leg between the flange and slot end 38. Stem 64 extends upwardly (FIG. 1) and acts as a radial spacer to prevent shank segments 42, 42 from being squeezed or deformed inwardly toward one another by the force exerted on them as nut 34 is tightened. This has been found desirable to prevent the connector from possibly "freezing" so that it cannot thereafter easily be moved to a desired position.

In use, connector assembly 20, including stud 24, bracket 22, stud slot insert 32, and nut 34 can be slid longitudinally along rod 14 to a desired position (note arrow 70 in FIG. 5). Until nut 34 is tightened the connector can be rotated circumferentially around the rod (arrow 71) and the bracket can be rotated (arrow 72) about the central axis of the stud, which extends perpendicularly to the rod. At a desired vertebral position laterally displaced from the rod 14, fastener 50 can be driven precisely into the spine where desired, through second opening 48 on the same side of the vertebrae as the rod 14. As previously noted, bracket 22 may be a flat bracket as shown, or it can be supplied with bends along various axes 54, 56, 58, so that the axis of opening 48 lies in a desired direction. The connector 20 can be used on a support in the form of a single rod 14; it is not limited to use with the double legged or U-shaped support shown, although that is preferred. The middle section 18 of support 12 (if a U-shaped support is used) can be screwed or otherwise secured to the skull. Wire attachments can also be used.

As previously noted, it is alternatively possible to insert a connector assembly 20 onto a rod 14 which has already been partially secured in place. For that purpose the slot insert 32 and nut 34 are removed, and the stud with the bracket on its shank is slipped laterally onto the leg 14. The spacer 32 is then seated on top of the rod, and the nut is secured. The stud can be slipped on the leg from the side and then rotated so that the nut is facing outward. Alternatively, the rod can be dropped into the slots of one or more connector studs with the brackets already secured to vertebrae.

This invention provides a significant improvement in vertebral fixation because it allows a physician to add one or more connectors on either or both legs of support 12, even after an operative procedure has started and the support has been mounted to the spine, if the physician determines that others are desirable. This can save substantial time and reduces the need for a highly prescribed mounting plan in advance. Although not shown in the drawings, the support rods 14, 16 may optionally extend downward across the cervicothoracic junction and may accept other connectors to secure it to lower spinal portions. Cross connectors between the rods can be used to improve the mechanical rigidity of the device. One or more lateral mass plates can also be positioned and secured to the same rods, in conjunction with this device, in order to secure cervical vertebrae.

Having described the invention, what is claimed is:

1. A spinal fixation device comprising:
   a rod adapted to extend along one side of selected vertebrae;
   a bracket having
      a first opening positioned to have said rod extend across said first opening, and
      a second opening;
   a stud having a head and a threaded shank, said shank extending rotatably through said first opening of said bracket with said head contacting one side of said bracket, and said shank having a longitudinal cross slot which extends toward said head with shank segments on opposite sides of said slot, said slot extending between said shank segments, said rod extending laterally through said slot in said stud and lying over an opposite side of said bracket;
   a fastener having a fastening shank extending through said second opening of said bracket, said fastener being rotatable with respect to said stud to move said fastener to a desired location for attachment into a vertebra at a position laterally displaced from said stud and on the one side of the selected vertebrae; and
   a nut threadable onto said shank segments of said stud for clamping said rod and said stud against rotation with respect to said bracket, thereby clamping said desired location of said fastener with respect to said stud.

2. The fixation device of claim 1 further comprising an insert within said slot of said stud, said insert being axially slidable in said slot and having a flange and a stem, said flange projecting laterally in said slot between said segments and bearing against said rod, said nut bearing against said flange to clamp said rod in said slot, said stem extending axially in said slot between said segments and projecting from said flange and into said nut, said stem holding said segments apart when said nut is tightened thereon.

3. The fixation device of claim 1 wherein said bracket further includes a first portion in which said first opening is presented and a second portion in which said second opening is presented, said second portion extending at an obtuse angle with respect to said first portion.

4. The fixation device of claim 1 wherein said insert is T-shaped; said flange extends outwardly beyond said shank to be engaged by said nut; and said stem extends axially in said slot.

5. The fixation device of claim 1 wherein said second opening is wider than said fastener, so that the axial direction of said fastener with respect to said bracket and stud can be changed.

6. The fixation device of claim 1 wherein said fastener is a bone screw.

7. The fixation device of claim 1 wherein said support is U-shaped with a middle section adapted to be secured to the occipital bone of a patient and two parallel rods adapted to be secured to the spinal column.

8. The fixation device of claim 1 wherein said slot extends to a slot end adjacent said head, and said slot end is contoured to facially engage said rod.

9. The fixation device of claim 1 wherein said bracket is recessed to receive said head of said stud.

10. The fixation device of claim 1 wherein said rod of said support has a groove around it in which a flexible vertebral attachment wire can be wrapped.

11. The fixation device of claim 10 wherein said groove is a spiral groove.

12. A spinal fixation device comprising:
   a vertebral support rod adapted to extend along one side of selected vertebrae;
   a bone fastener having a fastening shank;
   a bracket for adjustably connecting said fastener to said rod after said fastener has been inserted into a vertebra on the one side of the vertebrae
   and at a position laterally offset from said rod,
   said bracket having first and second openings, said fastener shank being longitudinally slidable through and rotatable in said second opening of said bracket for insertion into the vertebra, said bracket being connected to said rod by a stud having a head and a threaded shank, said shank extending through said first opening of said bracket with said head contacting one side of said bracket, and said shank having a cross slot which extends toward said head, said rod extending laterally through said slot of said stud and lying over an opposite side of said bracket, said slot separating shank segments on opposite sides of said slot, said bracket being rotationally positionable about said fastener and said stud, said stud being rotationally and longitudinally positionable along said rod; and a nut threadable onto said shank segments of said stud for clamping said rod and said stud against rotation with respect to said bracket, thereby clamping the position of said fastener with respect to said stud.

13. The fixation device of claim 12 further including an insert positioned within said slot of said stud, said insert bearing against said rod, said nut bearing axially against said insert, said insert holding said segments apart when said nut is tightened thereon.

14. The fixation device of claim 12 further including an insert positioned within said slot of said stud, said insert being axially slidable along said slot and having a flange and a stem, said flange projecting laterally in said slot between said segments and bearing against said rod, said nut bearing against said flange to clamp said rod in said slot, said stem extending axially in said slot between said segments and projecting perpendicularly from said flange and into said nut, said stem holding said segments apart within said nut when said nut is tightened thereon.

15. A spinal fixation device comprising:

a rod;

a bracket having
   a first opening positioned to have said rod extend across said first opening, and
   a second opening;

a stud having a head and a threaded shank, said shank extending rotatably through said first opening of said bracket with said head contacting one side of said bracket, and said shank having a longitudinal cross slot which extends toward said head with shank segments on opposite sides of said slot, said slot extending between said shank segments, said rod extending laterally through said slot in said stud and lying over an opposite side of said bracket;

a fastener having a fastening shank extending through said second opening of said bracket and into a vertebra, said fastener and bracket being rotatable with respect to said stud to move said fastener to a desired location for attachment into the vertebra; and a nut threadable onto said shank segments of said stud for clamping said rod and said stud against rotation with respect to said bracket, thereby clamping said desired location of said fastener with respect to said stud.

16. A spinal fixation device comprising:

a rod adapted to extend along one side of selected vertebrae;

a bracket having
   a first opening positioned to have said rod extend across said first opening, and
   a second opening;

a stud having a head and a threaded shank, said shank extending rotatably through said first opening of said bracket, and said shank having a longitudinal cross slot which extends toward said head with shank segments on opposite sides of said slot, said slot extending between said shank segments, said rod extending laterally through said slot in said stud;

a fastener having a fastening shank extending through said second opening of said bracket and into a vertebra at a position laterally displaced from said stud and on the one side of the selected vertabra, said fastener and bracket being rotatable with respect to said stud to move said fastener to a desired location for attachment into the vertebra; and a nut threadable onto said shank segments of said stud for clamping said rod and said stud against rotation with respect to said bracket, thereby clamping said desired location of said fastener with respect to said stud.

* * * * *